US00PP28773P3

(12) United States Plant Patent
Keithly

(10) Patent No.: US PP28,773 P3
(45) Date of Patent: Dec. 19, 2017

(54) RUSSETTED BARTLETT PEAR TREE

(50) Latin Name: *Pyrus communis*
Varietal Denomination: Russetted Bartlett

(71) Applicant: Stark Bro's Nurseries & Orchards Co., Louisiana, MO (US)

(72) Inventor: Doug Keithly, Yakima, WA (US)

(73) Assignee: Stark Bro's Nurseries & Orchards Co., Louisiana, MO (US)

( * ) Notice: Subject to any disclaimer, the term of this patent is extended or adjusted under 35 U.S.C. 154(b) by 0 days.

(21) Appl. No.: 14/757,006

(22) Filed: Nov. 6, 2015

(65) Prior Publication Data

US 2017/0135260 P1 May 11, 2017

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

U.S. PATENT DOCUMENTS

| | | | |
|---|---|---|---|
| PP741 | P | 7/1947 | Moritz |
| PP5,412 | P | 3/1985 | Brooks |
| PP5,468 | P | 5/1985 | Brooks |
| PP5,559 | P | 9/1985 | Brooks |
| PP5,573 | P | 10/1985 | Brooks |
| PP6,245 | P | 8/1988 | Reimer |
| PP6,362 | P | 11/1988 | Brooks |
| PP6,452 | P | 12/1988 | Ryugo |
| PP6,897 | P | 7/1989 | Zanzi |
| PP7,730 | P | 12/1991 | Lowry |
| PP10,325 | P | 4/1998 | Biehn et al. |
| PP17,387 | P3 | 1/2007 | White |
| PP17,624 | P3 | 4/2007 | Hart |

*Primary Examiner* — Annette Para

(74) *Attorney, Agent, or Firm* — Polster Lieder Woodruff & Lucchesi, L.C.

(57) ABSTRACT

A new and distinct cultivar of Bartlett pear tree named 'Russetted Bartlett' characterized particularly by producing fruit that has the overall appearance of a typical Bartlett pear, but is somewhat larger, totally russetted at maturity, and ripens later than typical Bartlett fruit.

4 Drawing Sheets

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a new and distinct cultivar of *Pyrus communis*, a pear tree, referred to by its cultivar name 'Russetted Bartlett'. 'A-Ri-Rang' Asian pears were planted with 'Williams bon chretien', commonly called the Bartlett pear tree, for the proper pollination of the Bartlett. One year later appearing in the top of a Bartlett tree were four pears looking like Bartlett but which were totally russetted. The following spring grafts were made to begin the 'Russetted Bartlett' Pear cultivar.

Discovery

The inventor grows pear trees in Yakima, Wash. The inventor grows Bartlett pear trees and has been growing Asian pears since 1989. Some cultivar of Asian pears are russetted. He has grown four real *Pyrus pyrifolia* cultivar: 'Hosui', 'A-Ri-Rang' (Korean Giant), *Pyrus pyrifolia* 'Singo' and *Pyrus pyrifolia* '20$^{th}$ Century' or 'Nijisseki'. The 'A-Ri-Rang' tree is a very large Korean cultivar that ripens very late, about November 5th or later in Yakima. He presently has about three (3) acres of Bartlett pear trees interspersed with 'A-Ri-Rang' pear trees. The Bartlett pears are naturally cross-pollinated by the 'A-Ri-Rang' cultivar. He discovered one limb on a cross-pollinated Bartlett pear that had four pears with the overall appearance and configuration of Bartlett pears but which were totally russetted. The inventor took limbs from the limb bearing the four 'Russetted Bartlett' pears and grafted them onto Bartlett pear rootstocks to asexually reproduce them, in Yakima, Wash. He thereby asexually reproduced trees that consistently bear a new cultivar of 'Russetted Bartlett' pears.

Propagation

The inventor took limbs from a limb bearing the four 'Russetted Bartlett' pears and grafted them. He thereby asexually reproduces trees that consistently bear the new cultivar of 'Russetted Bartlett' pears.

Uniqueness

The fruit, i.e. the pears from disclosed tree, have the overall configuration and appearance of its parent, a Bartlett pear, but are totally russetted at maturity, a unique copper color over the entire fruit. The size is slightly larger than such parental Bartlett pears and has a slightly sub-acid flavor. The instant 'Russetted Bartlett' pear ripens approximately a week later than its Barlett pear parent.

Use

The tree and its fruit were observed for a period of time and is believed to be particularly useful anywhere pear trees are raised; for example, in fruit trees orchards, field nurseries or in a landscape setting, and more particularly in these settings in the Pacific Northwest region of the United States.

Industry Representation

*Pyrus communis* and related varieties are disclosed in a number of plant patents including: U.S. Plant Pat. No. 741, Pear Tree; U.S. Plant Pat. No. 5,412, Pear Tree; U.S. Plant Pat. No. 5,468, Pear Tree; U.S. Plant Pat. No. 5,559, Pear Tree (Variety 69); U.S. Plant Pat. No. 5,573, Pear Tree; U.S. Plant Pat. No. 6,245, 'Reimer' Cultivar Pear Tree; U.S. Plant Pat. No. 6,362, Pear Tree Old Home×Farmingdale Variety No. 87; U.S. Plant Pat. No. 6,452 Pear Tree-'Elliot'; U.S. Plant Pat. No. 6,897, Pear Tree-'Red Winter'; U.S. Plant Pat. No. 7,730, 'Royal Forelle' Pear Tree; U.S. Plant Pat. No. 10,325, Pear Tree Named 'Biehn'; U.S. Plant Pat. No. 17,387, Pear Tree Named 'Prem2P'; and U.S. Plant Pat. No. 17,624, Pear Tree Named 'Prem1P'.

BRIEF SUMMARY OF THE VARIETY

The disclosed and claimed pear tree is a new distinct variety of Bartlett pear that has the overall configuration and attributes of a Bartlett pear, but is totally russetted. The present variety produces medium to large sized pear-shaped pome. The fruit has a typical golden base color with an overlay of russetting over the entire fruit when ripe. The flesh of the fruit is white and sweet when ripe.

BRIEF DESCRIPTION OF THE SEVERAL VIEWS OF THE DRAWINGS

The accompanying photographs depict the color of the flowers, foliage and fruit of my new variety as nearly as is reasonably possible to make the same in a color illustration of this character.

FIG. 1 is a photograph of a bowlful of the fruit of the new and distinct cultivar of Bartlett pear tree, 'Russetted Bartlett';

FIG. 2 is a photograph of a limb of 'Russetted Bartlett' showing blooms and leaves;

FIG. 3 is a photograph of limbs and leaves of the 'Russetted Bartlett'; and

FIG. 4 is a photograph of the cross-section of the fruit from the 'Russetted Bartlett'.

DESCRIPTION OF THE PREFERRED EMBODIMENT

The following is a detailed description of my new cultivar of 'Russetted Bartlett' Pear Tree with color terminology in accordance with The Royal Horticulture Society (R.H.S.) Colour Chart except where the context indicates a term having its ordinary dictionary meaning. My new tree has not been observed under all growing conditions and variations may occur as a result of different growing conditions. All progeny of my new variety cultivar of 'Russetted Bartlett' Pear tree, insofar as have been observed, have been identical in all the characteristics described below.

Other than as set forth below, as of this time, no other characteristics of my new 'Russetted Bartlett' Pear Tree have been observed by the inventor which are different from the characteristics common to Bartlett pear trees.

Parentage: A true sport limb first observed in 2009 included four (4) pears having the appearance of a Bartlett pear but being totally russetted. Using cuttings from that limb mutation additional trees were budded, creating a true sport limb of Bartlett.

Locality where grown and observed: Yakima, Wash.

Tree:

- *Size.*—Average for the species.
- *Vigor.*—Vigorous and hardy under typical climatic conditions around Yakima, Wash.
- *Tree form.*—Considered upright to upright spreading.
- *Tree height.*—When measured at the end of the 2014 growing season, the present variety had a height to about 3.66 to about 4.27 meters. This growth included to about 1.22 to 1.40 meters of the current season's growth.
- *Tree crown.*—Width — Approximately 1.4 meters. Trees of the present variety are growing in an orchard where spacing between the adjacent trees is about 1.83 meters, and the respective rows of trees are approximately 3.66 meters apart. The trees of the present variety are annually pruned into a narrow-upright vase training system.
- *Productivity.*—Productive.
- *Regularity of bearing.*—Regular annual.
- *Trunk diameter.*—When measured at a distance of approximately 20 centimeters from the ground level the variety has a trunk diameter of approximately 11 centimeters.

Bark:

- *Surface texture.*—Moderately cracked and roughened, some broad smooth areas are present.
- *Bark color.*—Considered light brown.
- *Bark lenticels.*—Numerous and appearing roughened on their surfaces. Bark lenticels shape: considered oval.
- *Lenticels.*—Size approximately 0.4 to about 0.9 millimeters in width, and from about 0.9 to about 2.5 millimeters in height. Lenticels color: creamy white.

Branches:

- *Size.*—Considered normal in diameter for the species. The main scaffold branches of the observed tree range in diameter from about 5 to about 7 centimeters when measured at the base of the scaffold.
- *Lenticels.*—Distinctive. The lenticels seen on the branches appear to have the same development as that of the trunk, noted above.
- *Upper branches.*—Size — The upper spreader branches range in size from about 5 to about 6.4 centimeters in diameter at their bases, while smaller hanger branches vary in thickness from about 0.79 to about 1.27 centimeters.
- *Surface texture.*—Scaffold branches appear smoother than the trunk surface, but have approximately the same brown color. (Fan #4, Sheet 164-C).
- *Older branches.*—Brown in color and nearly glabrous in surface texture. (Fan #4, Sheet 201B).

*One year old shoots and spurs.*—Color is considered brownish in color and having a moderately pubescent surface texture.

*Current season's shoots.*—Color is brown. These current season's shoots have a moderately pubescent surface texture.

*Actively growing shoots.*—Color is gray-brown. Actively growing shoots have a highly pubescent surface texture of medium length. The pubescence appears wooly.

*Expanding shoot tips and young leaves.*—Color is considered to be green in coloration.

*Internode length.*—When measured on upright vigorous shoots, this ranges from about 2.5 to 3.0 centimeters between adjacent nodes. The length between the nodes as seen on smaller lateral shoots ranges from about 1.5 to 2.0 centimeters.

Leaves:

*Size.*—Generally — Considered medium for the species. The measurements which follow have been taken from leaves growing near mid-shoot on vigorously growing current season's shoots.

*Leaf length.*—About 6.0 to about 8.0 centimeters including the leaf petiole.

*Leaf width.*—About 3.5 to about 5.0 centimeters.

*Leaf thickness.*—Medium. Considered normal for the species.

*Surface texture.*—Young immature leaves are highly pubescent on both the upper and lower leaf surfaces. As these leaves mature however, much of this pubescence is lost.

*Mature leaf texture.*—Very slightly rugose. No glands are evident on the leaf.

*Leaf form.*—Generally considered variable from broadly lanceolate to ovate.

*Leaf apices.*—Shape: Acute and at time curled backward from the upper leaf surface. Most leaves appear somewhat folded upwards.

*Leaf surface.*—Texture: The leaf surfaces along the mid-vein are at times slightly wavy.

*Leaf color.*—Mature leaves, the upper leaf surface appears dark green (Fan #3, Sheet 137-A); and the lower surfaces are a lighter green in color (Fan #3, Sheet 138-B).

*Color.*—Mid-Vein, the primary mid-vein on the lower leaf surface is a pale yellow-green (Fan #3, Sheet 145-C).

*Serrations.*—Size — Moderately small teeth.

*Leaf margins.*—Shape — Slightly undulate.

*Leaf margins.*—Generally considered serrate and tipped with narrow, soft, sharp spines.

*Leaf petiole.*—Size: Considered average and short, and further having a length of about 1.0 to 1.5 centimeters, and a thickness of about 1.0 to 1.5 millimeters when measured at approximately mid-petiole.

*Petiole base.*—Shape: Typically considered wider and at times slightly flared, and having a thickness of about 1.5 to 3.5 millimeters.

*Petiole.*—Color: Considered yellow-green on younger leaves (Fan #3, Sheet 144-D) and on older leaves a darker green shade (Fan #3, Sheet 145-C). Within the petiole groove and the petiole ridges, the color is increasingly darker (Fan #3, Sheet 138-B).

*Petiole.*—Surface texture is lightly pubescent.

*Immature leaves.*—Surface texture: Leaves appear to have a higher degree of pubescence than mature leaves. No glands are present on the petiole.

*Leaf stipules.*—Generally about 12 to 15 millimeters in length and about 0.75 to about 1.3 mm in width.

*Leaf stipules.*—Form: Considered linearly lanceolate. The leaf stipules darken and deteriorate within increasing senescence.

Flowers:

*Flower buds.*—Size — Generally considered large, plump and conic in form and are considered hardy under Yakima, Wash. climatic conditions.

*Flower buds.*—Color is reddish brown.

*Flower buds.*—Surface texture — Considered pubescent especially apically and over the interior side of the bud scales.

*Bloom time.*—Generally — Average to slightly early in relative comparison to other common Barlett pear tree varieties growing at the same geographic location.

*Date of full bloom.*—Observed at Yakima, Wash. on Mar. 27, 2014 and Mar. 27, 2015.

*Duration of bloom.*—The date and duration of bloom can be substantially effected by the amount of chilling hours that occur during a given year, and the geographical location where the variety is grown.

*Flower size.*—Generally about 28 to about 34 millimeters wide.

*Bloom quantity.*—Considered abundant.

*Flowers per node.*—As many as 6 can be produced.

*Petal numbers.*—Typically 5, but extra petals can be observed.

*Petal form.*—Considered variable, but most frequently appears round to ovate.

*Petal color.*—White (Fan #4, Sheet 155-D) with some pink shading around the margins.

*Petal margins.*—Shape — Undulate.

*Petal apices.*—Form — Variable and having a somewhat pointed tip.

*Flower pedicel.*—Size — These are variable from about 25 to about 30 millimeters in length, and from about 1.0 to about 1.5 millimeters in thickness.

*Flower pedicel.*—Color — Pale green (Fan #3, Sheet 145-C).

*Flower pedicel.*—Surface Texture — Pubescent, and further having moderately sparse filamentous pubescence.

*Floral nectaries.*—Color — Yellow-brown (Fan #3, Sheet 153-B). The floral nectaries become darker with increasing senescence.

*Calyx.*—Surface Texture — Slightly pubescent.

*Calyx.*—Color — Pale green (Fan #3, Sheet 145-B).

*Sepals.*—Surface Texture — Pubescent.

*Sepals.*—Size — Relatively small and narrow in form.

*Sepals.*—Color — Green-yellow (Fan #3, Sheet 151-B).

*Anthers.*—Size — Considered average for the species.

*Anthers.*—Color — Considered pale rose. This color appears both ventrally and dorsally.

*Pollen production.*—Considered abundant in quantity.

*Pollen.*—Color — yellow.

*Stamens.*—Color — White (Fan #4, Sheet 155-D) to pink about 4 to about 6 millimeters in length.

*Pistil.*—Form — The pistil of the present variety has five styles separated to the ovary.

*Pistil.*—Length — Somewhat variable from about 6 to 7 millimeters.

*Pistil.*—Surface Texture — Glabrous.

*Pistil.*—Color — Yellow-green (Fan #1, Sheet 1-D).

Fruit:

*Maturity when described.*—The fruit of the present variety of Bartlett pear tree is described at full commercial maturity hereinafter.

*Date of harvest.*—In 2013, the date of harvest was September 6. The date of harvest in 2014 was September 6. The date of harvesting is about September 1$^{st}$. The date of harvesting, noted above, are those that were observed at Yakima, Wash.

*Fruit size.*—Generally — The fruit diameter was about 30 to about 35 millimeters adjacent the stem and about 70 to about 80 millimeters around the base; the fruit had a height of about 100 to about 111 millimeters.

*Fruit form.*—Generally — Slightly variable classic pear shape when viewed in its lateral aspect.

*Fruit symmetry.*—Somewhat variable, from fully symmetrical to slightly asymmetrical or considered lopsided.

*Fruit stem.*—Size — The fruit stem has a length dimension of about 28 to about 32 millimeters; and a thickness dimension of about 2 to about 3 millimeters.

*Fruit stem.*—Shape — Typically, considered slightly curved.

*Fruit stem.*—Color — Light green (Fan #3, Sheet 144-B).

*Fruit stem.*—Surface Texture — Moderately pubescent.

*Fruit lenticels.*—Color — Light tan and being slightly raised and oval in form on the fruit stem surface (Fan #4, Sheet 161-A).

*Stem cavity.*—Shape — Considered uniform and acute.

*Stem cavity.*—Size — Considered moderate. The width of the stem cavity ranges from about 8 to about 10 millimeters when measured across the shoulders of the fruit. The depth of the stem cavity is variable from about 11 to about 15 millimeters.

*Fruit basin.*—Shape — Globose in form; relatively wide; and of average depth. The fruit basin sides are sloping and have what appears to be a smooth surface.

*Calyx.*—Form — The calyx opening is closed. Still further, the calyx tube is considered long and funnel shaped. Additionally, stamen remnants are often present in the calyx tube and are typically located in a marginal position.

*Core lines.*—Generally — These are distinct and clasping.

*Fruit core.*—Position — Distant and considered relatively far from the fruit stem.

*Fruit core.*—Size — Considered average in relation to the overall size of the fruit.

*Fruit carpels.*—Generally — 5 carpels are present and are located within the fruit core.

*Fruit carpels.*—Shape — star shaped.

*Fruit carpel cells.*—Form — Generally speaking, these are closed in form although at times some open cells can be present.

*Fruit carpels.*—Surface Texture — The inner surface of the carpel wall is considered glabrous.

*Seeds.*—Numbers — Variable from 2 to as many as 10.

*Seeds.*—Size — Considered plump, and having a length of about 8.5 to about 10.0 millimeters; and a width from about 3.5 to about 4.0 millimeters.

*Seeds.*—Thickness — About 3 millimeters.

*Seed apex.*—Form — Acute.

*Seeds.*—Color — Dark Brown at full maturity (Fan #4, Sheet 175-A). The seeds color at full commercial maturity is a lighter tan-brown color (Fan #4, Sheet 164-B).

*Fruit skin.*—Thickness — Considered average.

*Fruit skin.*—Surface texture — Glabrous. The skin appears to tightly adhere to the underlying fruit flesh.

*Fruit skin.*—Flavor — Considered mild to neutral.

*Fruit skin.*—Color — Predominately yellow-orange (Fan #1, Sheet 22-A) with russetting that can vary in hue and intensity over the entire surface of the fruit at full commercial maturity.

*Fruit skin.*—Lenticels — Few. These are small and relatively inconspicuous.

*Fruit skin lenticel color.*—Very pale yellow (Fan #1, Sheet 1-D).

*Fruit flesh.*—Color — White with a very slight cream-yellow tint (Fan #1, Sheet 11-D).

*Fruit flesh.*—Texture — Crisp and considered very juicy.

*Stone cells.*—Generally — Present, and average in number. The stone cells are located in the vicinity of the core area.

*Ripening.*—Considered even. The fruit holds well on the tree.

*Fruit flavor.*—Considered sweet, refreshing and mild, slightly sub-acid flavor and having a very good commercial quality.

*Aroma.*—Considered pleasant, and slight.

*Resistance to insects and diseases.*—No particular susceptibility where noted. The present variety has not been intentionally tested to expose or detect any susceptibilities or resistance to any known plant and/or other fruit tree diseases.

The invention claimed is:

1. What is claimed is a new and distinct cultivar of Bartlett pear tree named 'Russetted Bartlett' substantially as herein shown and described, particularly characterized over known Bartlett pear trees by producing fruit that has the overall appearance of a typical Bartlett pear, but is totally russetted at maturity. The russetted color is an attractive copper finish at full maturity and its ripening at about September 6$^{th}$ in Yakima, Wash. or about a week later as compared to regular Bartlett. 'Russetted Bartlett' is characterized by ability to be stored at 32° F. for approximately eight months while retaining its quality. Originator believes 'Russetted Bartlett' runs slightly larger than regular Bartlett. The fruit has an appealing slightly sub-acid flavor.

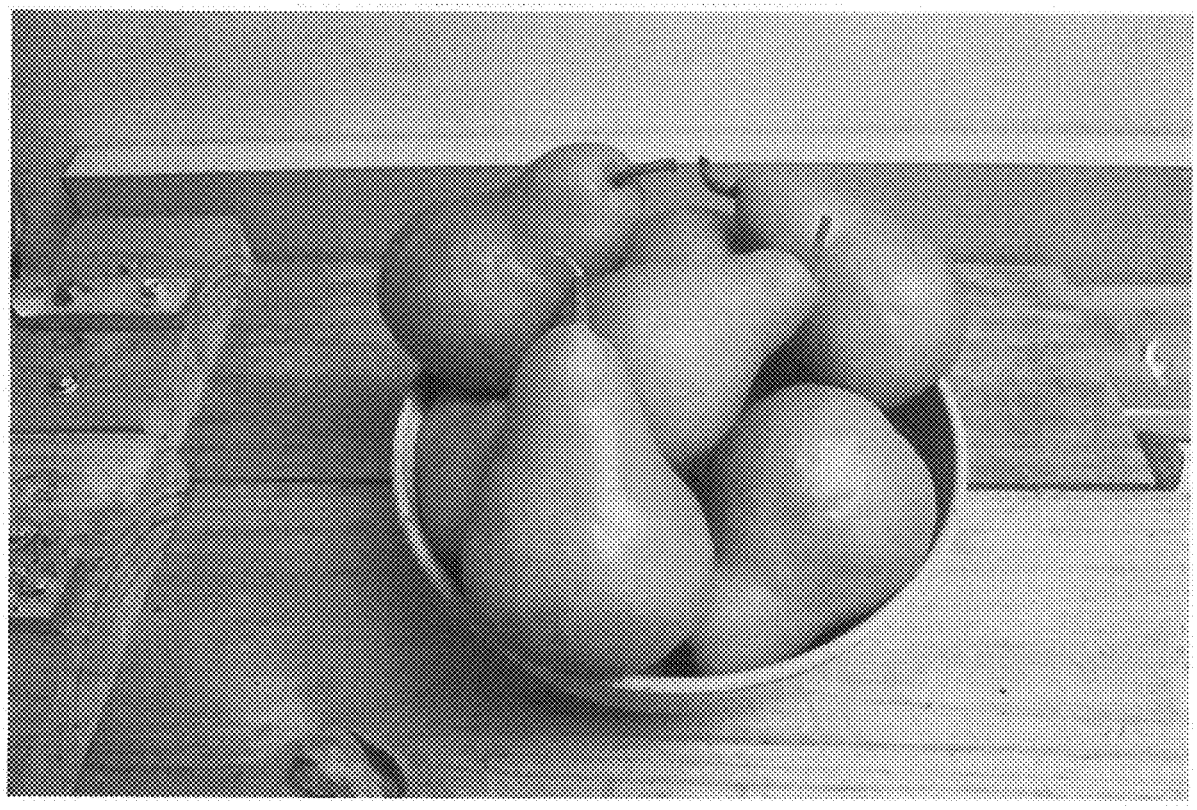

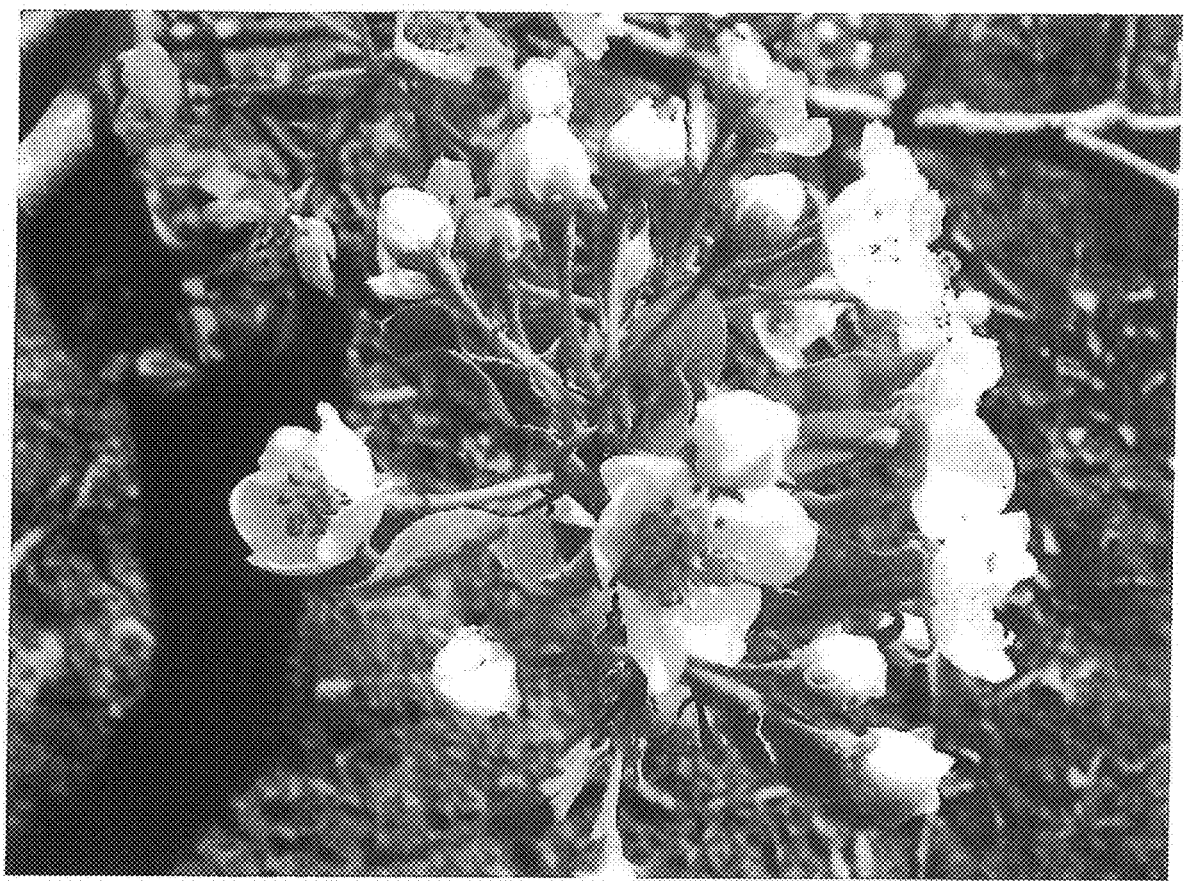

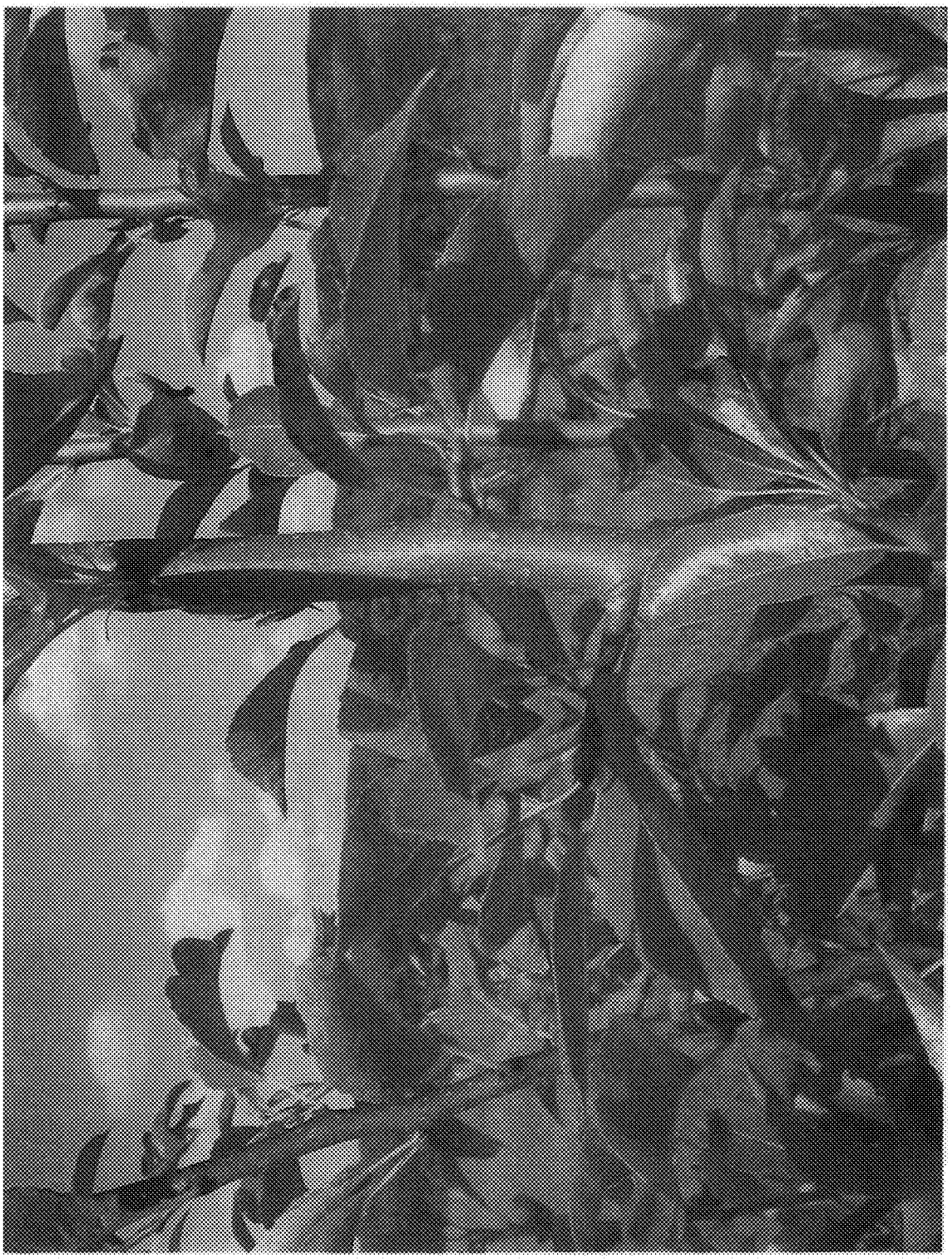

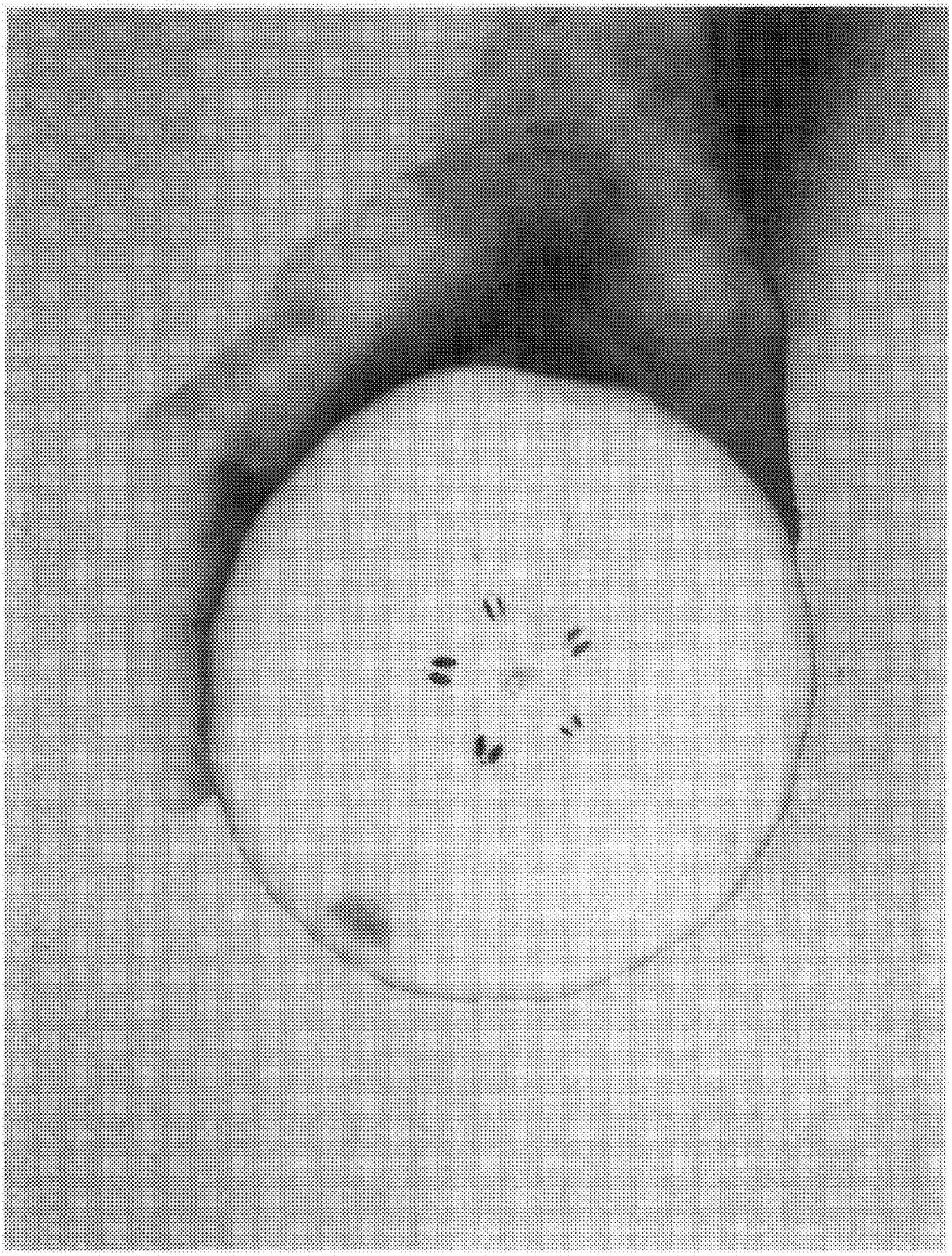

* * * * *